(12) United States Patent
Ullman et al.

(10) Patent No.: US 6,294,323 B1
(45) Date of Patent: Sep. 25, 2001

(54) SELF INITIATING SINGLE PRIMER AMPLIFICATION OF NUCLEIC ACIDS

(75) Inventors: Edwin F. Ullman, Atherton; Samuel J. Rose, Mountain View, both of CA (US)

(73) Assignee: Behringwerke AG, Marburg (DE)

( * ) Notice: Subject to any disclaimer, the term of this patent is extended or adjusted under 35 U.S.C. 154(b) by 0 days.

(21) Appl. No.: 08/046,682

(22) Filed: Apr. 14, 1993

(51) Int. Cl.[7] ............................ C07H 21/04; C12P 19/34; C12Q 1/68
(52) U.S. Cl. .......................... 435/6; 435/91.1; 435/91.2; 435/91.5; 435/15; 536/24.33; 935/77; 935/78
(58) Field of Search ......................... 435/6, 91.1, 91.2, 435/810, 91.5, 15; 935/77, 78, 91.1; 536/24.33

(56) References Cited

U.S. PATENT DOCUMENTS

| | | | |
|---|---|---|---|
| 4,358,535 | 11/1982 | Falkow et al. | 435/5 |
| 4,423,153 | 12/1983 | Ranney et al. | 436/63 |
| 4,480,040 | 10/1984 | Owens et al. | 436/504 |
| 4,486,539 | 12/1984 | Ranki et al. | 436/504 |
| 4,490,472 | 12/1984 | Gottlieb | 436/504 |
| 4,599,303 | 7/1986 | Yabusaki et al. | 435/6 |
| 4,647,529 | 3/1987 | Rodland et al. | 435/6 |
| 4,656,134 | 4/1987 | Ringold | 435/91 |
| 4,663,283 | 5/1987 | K'eid et al. | 435/91 |
| 4,675,283 | 6/1987 | Roninson | 435/6 |
| 4,677,054 | 6/1987 | White et al. | 435/6 |
| 4,683,195 | 7/1987 | Mullis et al. | 435/6 |
| 4,683,202 | 7/1987 | Mullis | 435/91 |
| 4,724,202 | 2/1988 | Dattagupta et al. | 435/6 |
| 4,800,159 | 1/1989 | Mullis et al. | 435/6 |
| 4,882,269 | 11/1989 | Schneider et al. | 435/6 |
| 4,908,307 | 3/1990 | Rodland et al. | 435/6 |
| 4,965,188 | 10/1990 | Mullis et al. | 435/6 |
| 5,008,182 | 4/1991 | Snisky et al. | 435/5 |
| 5,043,272 | 8/1991 | Hartley | 435/91 |
| 5,066,584 | 11/1991 | Gyllensten et al. | 435/91 |

FOREIGN PATENT DOCUMENTS

| | | |
|---|---|---|
| 904402 | 3/1986 | (BE) . |
| 0 164 054 A1 | 12/1985 | (EP) . |
| 0 185 494 A2 | 6/1986 | (EP) . |
| 0 194 545 A2 | 9/1986 | (EP) . |
| 0 200 362 A2 | 12/1986 | (EP) . |
| 0 302 175 A2 | 2/1989 | (EP) . |
| 0379369 | * 7/1990 | (EP) . |
| 0469755 | * 2/1992 | (EP) . |
| WO 89/12695 | 12/1989 | (WO) . |

OTHER PUBLICATIONS

Williams et al., Nuc. Acids Res. 18(22):6531–6535, Nov. 25, 1990.*
Welsh et al., Nuc. Acids Res. 19(2):303–306, Jan. 25, 1991.*
Welsh et al., Nuc. Acids Res. 19(19):5275–5279, Oct. 11, 1991.*

(List continued on next page.)

Primary Examiner—Stephanie W. Zitomer
Assistant Examiner—Paul B. Tran
(74) Attorney, Agent, or Firm—Theodore J. Leitereg; Rohan Peries

(57) ABSTRACT

A method is disclosed for producing at least one copy of a pair of complementary single stranded polynucleotides. The method comprises forming, in the presence of nucleoside triphosphates and template dependent polynucleotide polymerase along each of the complementary single stranded polynucleotides, an extension of a polynucleotide primer. The polynucleotide primer is comprised of at least a sequence of 16 nucleotides terminating at its 3' end in a 2 to 9 nucleotide sequence (S1), which is complementary with the 3' ends of both of the complementary single stranded polynucleotides. The polynucleotide primer has at least an 8 nucleotide sequence (S2) that is 5' of S1, where S2 is 50 to 80% complementary to the nucleotide sequences contiguous with the 3' ends of the complementary single stranded polynucleotides. The extended polynucleotide primer and the single stranded polynucleotides are then dissociated.

48 Claims, 4 Drawing Sheets

OTHER PUBLICATIONS

Welsh et al., Nuc. Acids Res. 20(19):4965–4970, Oct. 11, 1992.*

Sommer et al. Nuc. Acids Res. 17:6749, 1989.*

Bischofberger, et al., Nucleic Acids Research, (1987) vol. 15:2 pp. 709–716 "Cleavage of single stranded oligonucleotides by EcoRI restriction endonuclease".

Brigati, et al., Virology, (1983) vol. 126: pp. 32–50 "Detection of Viral Genomes in Cultured Cells and Paraffin–Embedded Tissue Sections Using Biotin–Labeled Hybridization Probes".

Bugawan, et al., Bio/Technology, (Aug. 1988) vol. 6: pp. 943–947 "The use of non–radioactive oligonucleotide probes to analyze enzymatically amplified DNA for prenatal diagnosis and forensic HLA typing".

de Jong, et al., Publication by Lawrence Livermore Labs, (PCR User Meeting Jan. 16, 1990, San Francisco, CA) "Isolation of Region–Specific Probes by ALU–PCR and Coincidence Cloning".

Fahrlander, et al., Bio/Technology, (Oct. 1988) vol. 6: pp. 1165–1168 "Amplifying DNA probe signals: A 'Christmas Tree' approach".

Frohman, et al., Proc. Natl. Acad. Science USA, (Dec. 1988) vol. 85, pp. 8998–9002 "Rapid production of full–length cDNAs from rare transcripts: Amplification using a single gene–specific oligonucleotide primer".

Goldkorn, et al., Nucleic Acids Research, (1986) vol. 14:22, pp. 9171–9191 "A simple and efficient enzymatic method for covalent attachment of DNA to cellulose. Application for hybridization–restriction analysis and for in vitro synthesis of DNA probes".

Langer, et al., Proc. Natl. Acad. Science USA, (Nov. 1981) vol. 78:11 pp. 6633–6637 "Enzymatic synthesis of biotin-labeled polynucleotides: Novel nucleic acid affinity probes".

Lizardi, et al., Bio/Technology, (Oct. 1988) vol. 6: pp. 1197–1202 "Exponential amplification of recombinantRNA hybridization probes".

Nelson, et al., Proc. Natl. Acad. Science USA, (Sep. 1989) vol. 86: pp. 6686–6690 Alu Polymerase chain reaction: A method for rapid isolation of human–specific sequences from complex DNA sources.

Paabo, et al., The Journal of Biological Chemistry, (1990) vol. 265:8 pp. 4718–4721 "DNA Damage Promotes Jumping between Templates during Enzymatic Amplification".

Parks, et al., Nucleic Acids Research, (1991) vol. 19:25 pp. 7155–7160 "A polymerase chain reaction mediated by a single primer: cloning of genomic sequences adjacent to a serotonin receptor protein coding region".

Saiki, et al. Science, (Dec. 1985) vol. 230: pp. 1350–1354 "Enzymatic Amplification of β–Globin Genomic Sequences and Restriction Site Analysis for Diagnosis of Sickle Cell Anemia".

Saiki, et al. Science, (Jan. 1988) vol. 239 pp. 487–491 "Primer–Directed Enzymatic Amplification of DNA with a Thermostable DNA Polymerase".

Strobel, et al., Molecular and Cellular Biology, (Jul. 1986) vol. 6:7 pp. 2674–2683 "Intron Mutations Affect Splicing of *Saccharomyces cerevisiae* SUP53 Precursor tRNA".

Stoflet, et al., Science, (Jan. 1988) vol. 239 pp. 491–494 "Genomic Amplification with Transcript Sequencing".

Timblin, et al., Nucleic Acids Research, (1990) vol. 18:6, pp. 1587–1593 "Application for PCR technology to subtractive cDNA cloning: identificatin of genes expressed specifically in murine plasmacytoma cells".

Wang, et al., DNA and Cell Biology, (1991) vol. 10:10 pp. 771–777 "Single Primer–Mediated Polymerase Chain Reaction: Application in Cloning of Two Different 5'–Untranslated Sequences of Acidic Fibroblast Growth Factor mRNA".

Watson, et al., Molecular Biology of the Gene, Fourth Edition, The Benjamin/Cummings Publishing Co. Inc., Menlo Park, CA pp. 939–941 "Reverse Transcriptase Generates Long Terminal Repeats in Proviral DNA".

* cited by examiner

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Synthetic (xi) SEQUENCE DESCRIPTION: SEQ ID NO:1:

CTCGCTTGAA AAGAGTATAT GGCCAGTCTT GCGGG    35

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Synthetic (xi) SEQUENCE DESCRIPTION: SEQ ID NO:2:

CTCGCTTTAA AATGAGATAT TTTCAGTCAA ACGGG                35

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:3:

ACGCGAATCA GTTAAAACAT TCATCTATGA CCCCC                35

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:4:

GTAAGAGCAA CACTATCATA A                              21

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (xi) SEQUENCE DESCRIPTION: SEQ ID NO:5:

GATTCAGCAA TTAAGCTCTA AGCC                           24

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

-continued (iii) HYPOTHETICAL: NO (iv) ANTI-SENSE: NO (vi) ORIGINAL SOURCE:
         (A) ORGANISM: Synthetic (xi) SEQUENCE DESCRIPTION: SEQ ID NO:6:

TACAGTTCCT CGTCAGTCTT AACAGCACCC GATTT                    35

(2) INFORMATION FOR SEQ ID NO:7:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Synthetic (xi) SEQUENCE DESCRIPTION: SEQ ID NO:7:

TTACATTTTC TCGCGTATCT GCAACGCACT GTATT                    35

SELF INITIATING SINGLE PRIMER AMPLIFICATION OF NUCLEIC ACIDS

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}$P labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very concentrations of disease related DNA or RNA present in a patient's body fluid and the unavailability of a sufficiently sensitive method of nucleic acid hybridization analysis.

Commonly used methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The presence of hybridized material on the support is detected by autoradiography or by spectrometric methods.

Since these methods are slow and labor intensive, and generally not suitable for very low concentrations, it is desirable to develop methods with increased sensitivity and simplicity. Preferably, new methods should avoid the hazards of radioactivity and employ homogeneous assay techniques, which offer opportunities for speed and simplicity.

Recently, a method for the enzymatic amplification of specific double stranded sequences of DNA known as the polymerase chain reaction (PCR) has been described. This in vitro amplification procedure is based on repeated cycles of denaturation, oligonucleotide primer annealing, and primer extension by thermophilic polymerase, resulting in the exponential increase in copies of the desired sequence flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method that has recently been described is an amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may be already part of a polynucleotide analyte or may be created as the result of the presence of a polynucleotide.

One aspect of single primer amplification as it is currently described is that, if a single strand of the analyte is not capable of forming a stem-loop structure, then a single stranded polynucleotide having such a stem-loop structure must be created. This created single stranded polynucleotide must also be related to the presence of the polynucleotide analyte. The present invention allows for the advantages of single primer amplification, namely one primer and one polymerase, without the need for this added step of creating a single stranded polynucleotide with a stem-loop structure.

2. Description of the Related Art.

A polymerase chain reaction mediated by a single primer: cloning of genomic sequences adjacent to a serotonin receptor protein coding region is described by Parks, et al., *Nucleic Acids Research* (1991) 19(No.25): 7155–7160. Wang, et al., *DNA and Cell Biology* (1991) 10(No.10): 771–777 discuss the single primer-mediated polymerase chain reaction: application in cloning of two different 5'-untranslated sequences of acidic fibroblast growth factor mRNA.

Paabo, et al., discuss jumping between templates during enzymatic amplification promoted by DNA damage (*J. Biol. Chem.* (1990) 265(No.8): 4718–4721).

U.S. patent application Ser. Nos. 07/299,282 and 07/399,795 filed Jan. 19, 1989, and Aug. 29, 1989, respectively, describe nucleic acid amplification using a single polynucleotide primer. U.S. patent application Ser. No. 07/555,323 filed Jul. 19, 1990, discloses methods for producing a polynucleotide for use in single primer amplification. U.S. patent application Ser. No. 07/555,968 filed Jul. 19, 1990, describes a method for producing a molecule containing an intramolecular base-pair structure. U.S. patent application Ser. No. 07/776,538 filed Oct. 11, 1991, discloses methods for producing a polynucleotide for use in single primer amplification. U.S. patent application Ser. No. 07/923,079 filed Jul. 31, 1992, describes a method for introducing sequences at the 3' end of polynucleotides. The disclosures of these six applications are incorporated herein by reference in their entirety.

A process for amplifying, detecting and/or cloning nucleic acid sequences otherwise referred to as PCR is disclosed in U.S. Pat. Nos. 5,008,182, 4,965,188, 4,800,159, 4,683,195 and U.S. Pat. No. 4,683,202. Sequence polymerization by PCR is described by Saiki, et al., (1986) *Science,* 230: 1350–1354.

Rapid production of full-length cDNAs from rare transcripts: amplification using a single gene-specific oligonucleotide primer is discussed by Frohman, et al., in *Proc. Natl. Acad. Sci. USA* (1988) 85:8998–9002. A discussion of the generation of long terminal repeats in proviral DNA by reverse transcriptase is found in "Molecular Biology of the Gene," Fourth Edition, The Benjamin/Cummings Publishing Company, Inc., Menlo Park, Calif., pages 939–941. The effect of intron mutations on the splicing of *Saccharomyces cerevisiae* SUP53 precursor tRNA is discussed by Strobel, et al., in *Molecular and Cellular Biology* (1986) 6(No.7): 2674–2683. Amplification of nucleic acid sequences using oligonucleotides of random sequence as primers is described in U.S. Pat. No. 5,043,272.

A single stranded self-hybridizing nucleic acid probe capable of repeatedly hybridizing to itself or other nucleic acids to form an amplified entity is described in U.S. patent application Ser. No. 888,058, filed Jul. 22, 1986 (Department of Health and Human Services). Methods of generating single stranded DNA by PCR are disclosed in U.S. Pat. No. 5,066,584. A method of making an oligonucleotide is described in European Patent Application No. 0194545 A2. Belgian Patent Application No. BE 904402 discloses a mold for making DNA detection probes. Gene amplification in eukaryotic cells is disclosed in U.S. Pat. No. 4,656,134.

Langer, et al., *Proc. Natl. Acad. Sci. USA,* (1981) 78: 6633–6637 discloses the enzymatic synthesis of biotin labelled polynucleotides and the use of these materials as novel nucleic acid affinity probes. The detection of viral genomes in cultured cells and paraffin imbedded tissue sections using biotin labelled hybridization probes is discussed by Brigati, et al., *Virology,* (1983) 126: 32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European Patent Application No. 106 112 (Priority U.S. patent application 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European Patent Application No. 0164054 A1. U.S. Pat. No. 4,663,283 describes a method of altering double-stranded DNA.

Genomic amplification with transcript sequencing is discussed by Stoflet, et al., *Science* (1988) 239:491. Primer-directed enzymatic amplification of DNA with a thermostable DNA polymerase is described by Saiki, et al., *Science* (1988) 239:487. U.S. Pat. No. 4,724,202 discloses the use of non-hybridizable nucleic acids for the detection of nucleic acid hybridization. Bugawan, et al., *Bio/Technology,* (1988) 6:943–947 describe the use of non-radioactive oligonucleotide probes to analyze enzymatically amplified DNA for prenatal diagnosis and forensic HLA typing.

Detection and isolation of homologous, repeated and amplified nucleic acid sequences is disclosed in U.S. Pat. No. 4,675,283. European Patent Application No. 0200362 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14: 9171–9191. Cleavage of single stranded oligonucleotides by Eco RI restriction endonuclease is described in *Nucleic Acids Research* (1987) 15: 709–716.

Exponential Amplification of Recombinant-RNA Hybridization Probes is described by Lizardi, et al. (1988) *Bio/Technology* 6:1197–1202. Fahrlander, et al., discusses Amplifying DNA Probe Signals: A Christmas Tree Approach in *Bio/Technology* (1988) 6:1165–1168. A nucleic acid hybridization assay employing probes cross-linkable to target sequences is described in U.S. Pat. No. 4,599,303.

A hybridization method and probe for detecting nucleic acid sequences is described in U.S. Pat. No. 4,908,307. An amplified hybridization assay is described in U.S. Pat. No. 4,882,269 wherein a family of signal-generating secondary probes bind to a primary probe that hybridizes to the target sequence of interest.

Detection of target sequences in nucleic acids by hybridization using diagnostic and contiguous probes for diagnosis of genetic abnormality diseases, especially in an automated procedure, is described in European Patent Application No. 0 185 494A2.

International Patent Application No. PCT/US89/02646 describes DNA amplification and subtraction techniques. Timblin, et al., discuss the application of PCR technology to subtractive DNA cloning and the identification of genes expressed specifically in murine plasmacytoma cells in *Nucleic Acids Research* (1990) 18(No.6): 1587–1593. Nelson, et al., disclose Alu PCR as a method for rapid isolation of human-specific sequences from complex DNA sources in *Proc. Natl. Acad. Sci. USA* (1989) 86: 6686–6690. The isolation of region-specific probes by Alu-PCR and coincidence cloning is discussed by de Jong, et al., in a publication of Lawrence Livermore Labs (1990).

SUMMARY OF THE INVENTION

In one embodiment of the present invention a method is described for producing at least one copy of a pair of complementary single stranded polynucleotide sequences. The method comprises forming, in the presence of nucleoside triphosphates and template dependent polynucleotide polymerase along each of the complementary single stranded polynucleotide sequences, an extension of a single polynucleotide primer. The polynucleotide primer is comprised of at least a sequence of 16 nucleotides terminating at its 3' end in a 2 to 9 nucleotide sequence (S1) that is complementary with the 3' ends of both of the complementary single stranded polynucleotide sequences. The polynucleotide primer has a specifically designed sequence of at least 8 nucleotides (S2) that is 5' of S1, where S2 is 50 to 80% complementary to each of the nucleotide sequences contiguous with the 3' ends of the complementary single stranded polynucleotide sequences. The extended polynucleotide primer and the single stranded polynucleotides are then dissociated.

In another embodiment of a method in accordance with the invention, multiple copies of a polynucleotide sequence and its complement are produced. The method comprises providing in combination (1) a pair of complementary single stranded polynucleotides having the polynucleotide sequence and its complement, (2) a single polynucleotide primer being comprised of at least a sequence of 16 nucleotides terminating at its 3' end in a 2 to 9 nucleotide sequence (S1) that is complementary with the 3' ends of both the polynucleotide sequence and its complement, wherein the polynucleotide primer has a specifically designed sequence of at least 8 nucleotides (S2) that is 5' of S1, wherein S2 is 50 to 80% complementary to each of the nucleotide sequences contiguous with the 3' ends of the polynucleotide sequence and its complement, (3) nucleoside triphosphates, (4) template dependent polynucleotide polymerase. The combination is incubated under conditions for either wholly or partially sequentially or concomitantly (1) dissociating the polynucleotide sequence and its complement, (2) hybridizing the polynucleotide primer with the sequence at the 3' end of the polynucleotide sequence and its complement, (3) extending the polynucleotide primer along the polynucleotide sequence and its complement to provide a first complementary pair of extended polynucleotide primers, (4) dissociating the first complementary pair of extended polynucleotide primers from the polynucleotide sequence and its complement, (5) hybridizing single stranded extended polynucleotide primers from the first complementary pair with the polynucleotide primer, (6) extending the polynucleotide primer along the single stranded extended polynucleotide primers to provide a second complementary pair of extended polynucleotide primers, (7) dissociating the second complementary pair of extended polynucleotide primers from the first complementary pair of extended polynucleotide primers, and (8) repeating steps (5)–(7) above.

Another embodiment of the invention is a method for determining the presence of a polynucleotide analyte in a sample suspected of containing the analyte. The analyte has complementary single stranded polynucleotide sequences that, together with nucleotide sequences contiguous with the 3' ends of the complementary single stranded polynucleotide sequences, are at least partially known. In the method a combination is provided comprising (1) the sample, (2) a polynucleotide primer comprised of at least a sequence of 16 nucleotides terminating at its 3' end in a 2 to 9 nucleotide sequence (S1) that is complementary with the 3' ends of both of the complementary single stranded polynucleotide sequences, wherein the polynucleotide primer has a specifically designed sequence of at least 8 nucleotides (S2) that is 5' of S1, wherein S2 is 50 to 80% complementary to each of the nucleotide sequences contiguous with the 3' ends of the complementary single stranded polynucleotide sequences, (3) nucleoside triphosphates and (4) template dependent polynucleotide polymerase. The combination is incubated under conditions for either wholly or partially sequentially or concomitantly (1) dissociating complementary sequences of the analyte into single stranded polynucleotides, (2) hybridizing the polynucleotide primer with the 3' end of the single stranded polynucleotide sequences, (3) extending the polynucleotide primer along the single stranded polynucleotides to provide a first complementary pair of extended polynucleotide primers, (4) dissociating the first complementary pair of extended polynucleotide primers from the single stranded polynucleotide sequences, (5) hybridizing single stranded extended polynucleotide primers from the first complementary pair with the polynucleotide primer, (6) extending the polynucleotide primer along the single stranded extended polynucleotide primers to provide a second complementary pair of extended polynucleotide primers, (7) dissociating the second complementary pair of extended polynucleotide primers from the single stranded extended polynucleotide primers, and (8) repeating steps (5)–(7) above. Steps (a) and (b) are performed wholly or partially sequentially or concomitantly. An examination for the presence of extended polynucleotide primers is conducted, the presence thereof indicating the presence of the polynucleotide analyte.

Another embodiment of the invention concerns a combination of a pair of complementary single stranded polynucleotide sequences and a single polynucleotide being in at least 1000-fold excess of said pair of complementary single stranded polynucleotide sequences and being comprised of (1) an 8 to 48 nucleotide sequence that is 50–80% complementary to nucleotide sequences contiguous with each of the 3' ends of the complementary single stranded polynucleotide sequences and (2) a 2 to 9 nucleotide sequence at the 3' end of the 8 to 48 nucleotide sequence that is complementary to the 3' ends of both of the single stranded polynucleotide sequences.

The invention further includes kits for use in determining a polynucleotide analyte. The analyte has complementary single stranded polynucleotide sequences, which have at least partially known 3' end sequences, that are characteristic for the analyte. The kit comprises in packaged combination (a) a polynucleotide primer comprised of at least a sequence of 16 nucleotides terminating at its 3' end in a 2 to 9 nucleotide sequence (S1), which is complementary with the 3' ends of both of the complementary single stranded polynucleotides of the analyte, wherein the polynucleotide primer has at least an 8 nucleotide sequence (S2) that is 5' of S1, wherein S2 is 50 to 80% complementary to the nucleotide sequences contiguous with the 3' ends of the complementary single stranded polynucleotides, (b) nucleoside triphosphates and (c) template dependent polynucleotide polymerase.

DESCRIPTION OF THE SPECIFIC EMBODIMENTS

Figure 1:
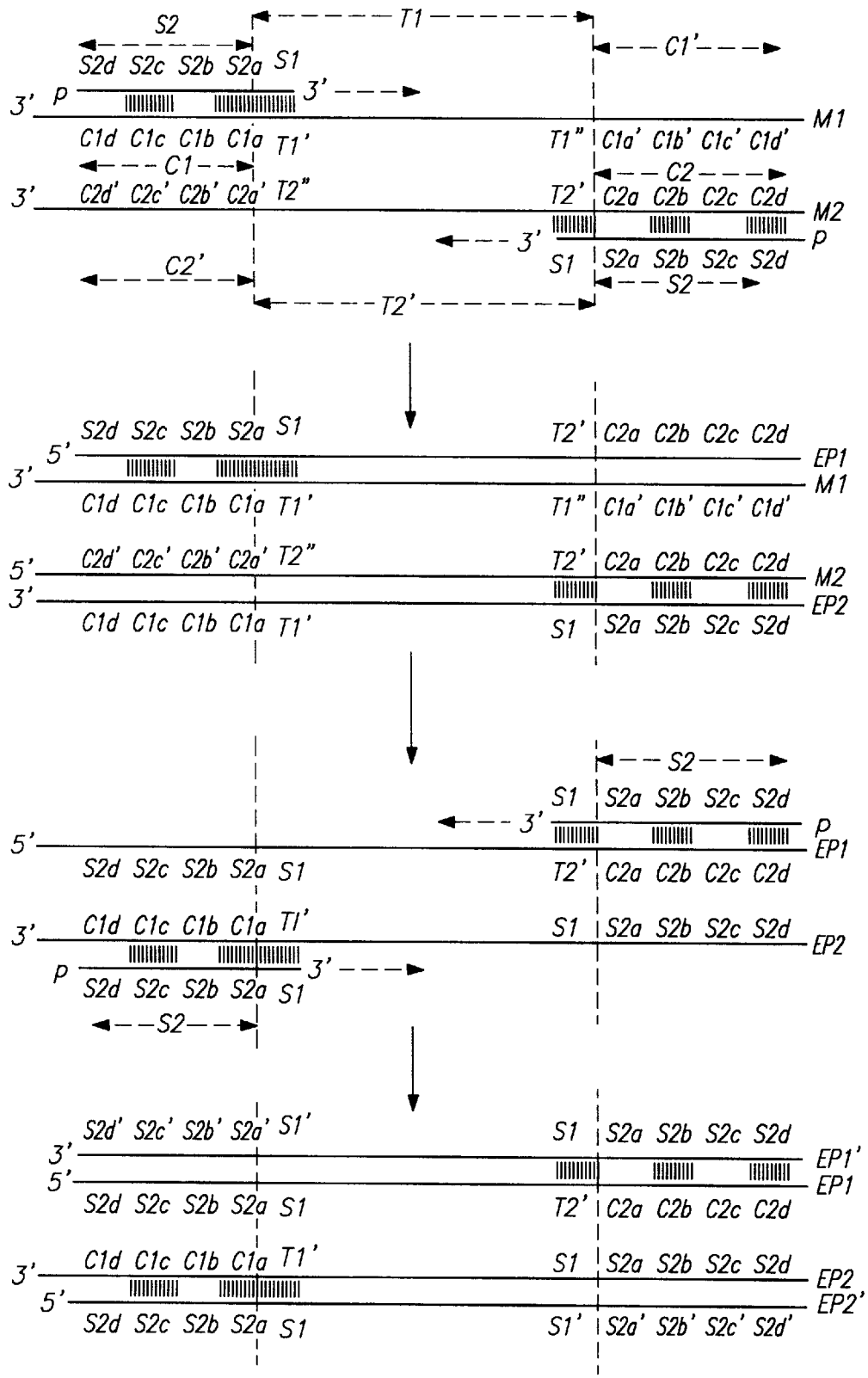
FIG. 1 is a schematic of an embodiment in accordance with the present invention.

The present method allows for initiation of amplification of a target polynucleotide sequence using single primer amplification in which a single polydeoxynucleotide primer is extended along both single strands from a dissociated pair of complementary strands of a polynucleotide. The present method differs from other methods of initiating single primer amplification in that in the present method the single primer can be initially extended along both single strands from a double stranded target molecule. In some of the known methods of initiation of single primer amplification, the single primer is extended initially along only one of the single strands from a double stranded target. The instant invention differs from the methods of Parks, et al., and Wang, et al., in that the methods of these references are applied to the attempted amplification of unknown sequences. In these reference methods a primer is employed that in a chance happening may hybridize to both of the strands of the DNA. In the present invention the sequence must be known and the primer is specifically designed to hybridize to sequences in both strands.

As a result of the present invention it is unnecessary to construct from the target a special single stranded polydeoxynucleotide that is capable of being amplified by single primer amplification. The known method requires initially the formation of a single stranded polydeoxynucleotide that has a structure capable of intramolecular base-pairing, i.e., having two segments that are non-contiguous and complementary with each other, otherwise known as an inverted repeat, which can form a stem-loop structure. The instant method has particular application in the area of single primer amplification in which a target polynucleotide sequence in a sample is amplified when such target polynucleotide sequence does not have a structure capable of intramolecular base-pairing. The present method provides a highly convenient method for amplifying a polynucleotide sequence of interest with a minimum number of reagents and steps. In the present method only one primer and one polymerase are used. The method involves designing an appropriate primer based on the structure of the nucleic acid to be amplified. The primer is designed so that it will hybridize to both dissociated strands of a double stranded molecule and under appropriate conditions be extended along both of the strands to produce extended primer that comprises the sequence of interest.

Before proceeding further with a description of the specific embodiments of the present invention, a number of terms will be defined.

Polynucleotide analyte—a compound or composition to be measured that is a polymeric nucleotide or a portion of a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation of the polymeric nucleotide. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

Microorganisms of interest include:

Corynebacteria

Corynebacterium diphtheria
Pneumococci

Diplococcus pneumoniae
Streptococci

Streptococcus pyrogenes
Streptococcus salivarus
Staphylococci

Staphylococcus aureus
Staphylococcus albus
Neisseria

Neisseria meningitidis
Neisseria gonorrhea
Enterobacteriaciae

Escherichia coli
Aerobacter aerogenes           The colliform
Klebsiella pneumoniae          bacteria
Salmonella typhosa             The Salmonellae TABLE I-continued Microorganisms of interest include:

Salmonella choleraesuis
Salmonella typhimurium
Shigella dysenteria            The Shigellae
Shigella schmitzii
Shigella arabinotarda
Shigella flexneri
Shigella boydii
Shigella sonnei
Other enteric bacilli Proteus vulgaris               Proteus species
Proteus mirabilis
Proteus morgani
Pseudomonas aeruginosa
Alcaligenes faecalis
Vibrio cholerae
Hemophilus-Bordetella group    Rhizopus oryzae Hemophilus influenza, H. ducryi   Rhizopus arrhizua Phycomycetes
Hemophilus hemophilus             Rhizopus nigricans
Hemophilus aegypticus             Sporotrichum schenkii
Hemophilus parainfluenza          Flonsecaea pedrosoi
Bordetella pertussis              Fonsecacea compact
Pasteurellae                      Fonsecacea dermatidis Pasteurella pestis                Cladosporium carrionii
Pasteurella tulareusis            Phialophora verrucosa
Brucellae                         Aspergillus nidulans Brucella melitensis               Madurella mycetomi
Brucella abortus                  Madurella grisea
Brucella suis                     Allescheria boydii
Aerobic Spore-forming Bacilli     Phialophora jeanselmei Bacillus anthracis                Microsporum gypseum
Bacillus subtilis                 Trichophyton mentagrophytes
Bacillus megaterium               Keratinomyces ajelloi
Bacillus cereus                   Microsporum canis
Anaerobic Spore-forming Bacilli   Trichophyton rubrum Clostridium botulinum             Microsporum adouini
Clostridium tetani                Viruses Clostridium perfringens           Adenoviruses
Clostridium novyi                 Herpes Viruses Clostridium septicum              Herpes simplex
Clostridium histolyticum          Varicella (Chicken pox)
Clostridium tertium               Herpes Zoster (Shingles)
Clostridium bifermentans          Virus B
Clostridium sporogenes            Cytomegalovirus
Mycobacteria                      Pox Viruses Mycobacterium tuberculosis        Variola (smallpox)
hominis                           Vaccinia
Mycobacterium bovis               Poxvirus bovis
Mycobacterium avium               Paravaccinia
Mycobacterium leprae              Molluscum contagiosum
Mycobacterium paratuberculosis    Picornaviruses Actinomycetes (fungus-like bacteria)   Poliovirus Actinomyces Isaeli                Coxsackievirus
Actinomyces bovis                 Echoviruses
Actinomyces naeslundii            Rhinoviruses
Nocardia asteroides               Myxoviruses Nocardia brasiliensis             Influenza (A, B, and C)
The Spirochetes                   Parainfluenza (1–4)

Treponema pallidum Spirillum minus    Mumps Virus
Treponema pertenue Streptobacillus    Newcastle Disease Virus
monoilifformis                        Measles Virus
Treponema carateum                    Rinderpest Virus
Borrelia recurrentis                  Canine Distemper Virus
Leptospira icterohemorrhagiae         Respiratory Syncytial Virus
Leptospira canicola                   Rubella Virus TABLE I-continued Microorganisms of interest include:

| | |
|---|---|
| Trypanasomes | Arboviruses |
| Mycoplasmas | Eastern Equine Eucephalitis Virus |
| Mycoplasma pneumoniae | Western Equine Eucephalitis Virus |
| Other pathogens | Sindbis Virus |
| Listeria monocytogenes | Chikugunya Virus |
| Erysipelothrix rhusiopathiae | Semliki Forest Virus |
| Streptobacillus moniliformis | Mayora Virus |
| Donvania granulomatis | St. Louis Encephalitis Virus |
| Bartonella bacilliformis | California Encephalitis Virus |
| Rickettsiae (bacteria-like parasites) | Colorado Tick Fever Virus |
| Rickettsia prowazekii | Yellow Fever Virus |
| Rickettsia mooseri | Dengue Virus |
| | Reoviruses |
| Rickettsia rickettsii | Reovirus Types 1–3 |
| Rickettsia conori | Retroviruses |
| Rickettsia australis | Human Immunodeficiency Viruses |
| Rickettsia sibiricus | Human T-cell Lymphotrophic |
| Rickettsia akari | Virus I & II (HTLV) |
| (HIV) | Hepatitis |
| Rickettsia tsutsugamushi | Hepatitis A Virus |
| Rickettsia burnetti | Hepatitis B Virus |
| Rickettsia quintana | Hepatitis nonA-nonB Virus |
| Chlamydia (unclassifiable parasites | Tumor Viruses |
| bacterial/viral) | Rauscher Leukemia Virus |
| Chlamydia agents (naming uncertain) | Gross Virus |
| Fungi | Maloney Leukemia Virus |
| Cryptococcus neoformans | Human Papilloma Virus |
| Blastomyces dermatidis | |
| Hisoplasma capsulatum | |
| Coccidioides immitis | |
| Paracoccidioides brasiliensis | |
| Candida albicans | |
| Aspergillus fumigatus | |
| Mucor corymbifer | |
| (Absidia corymbifera) | |

The polynucleotide analyte, where appropriate, may be treated to cleave the analyte to obtain a polynucleotide fragment that contains a target polynucleotide sequence. Such cleaving treatment with a restriction endonuclease or other site specific chemical cleavage method. However, it is an advantage of the present invention that the polynucleotide analyte can be used in its isolated state without further cleavage. The cleaved polynucleotide fragment may be referred to herein as a polynucleotide analyte.

For purpose of this invnetion, the polynucleotide analyte, or a cleaved fragment obtained from the polynucleotide analyte, is usually at least partially denatured or single stranded. Such treatments are well-known in the art and include, for instance, heat or alkali at 90–100° C. for a period of 10–20 seconds or more, produces denatured material.

Target polynucleotide sequence—a sequence of nucleotides to be identified, either RNA or DNA, existing within a polynnucleotide analyte. The target polynucleotide sequence is at least 100 nucleotides, usually at least 200, frequently 200–4000 nucleotides, in lenght. Preferably the target polynucleotide sequence is about 200 to 1200 deoxynucleotides.

The minimum number of nucleotides in the target polynucleotide sequence is selected to assure that the presence of target polynucleotide sequence in a medium is a specific indicator of the presence of polynucleotide analyte in a sample. The maximum number of nucleotides in the target polynucleotide sequence is normally governed by the efficiency of amplification of the sequence but may be also limited by the length of the polynucleotide analyte, and its tendency to be broken by shearing, or other processes during isolation and any procedures required to prepare the sample for assay.

Single stranded (ss) polynucleotide sequence—one of two complementary strands of a polynucleotide sequence of a polynucleotide analyte. Generally, the nucleotide sequence of the polynucleotide analyte is known at least with respect to 2 to 9 nucleotides at the 3' ends and sequences of 8 to 60, preferably, 12 to 45, nucleotides contiguous with the 3' ends of the single stranded polynucleotide sequence. These contiguous known sequences together with the single stranded polynucleotide sequences comprise the target polynucleotide sequence.

Polynucleotide primer—a polynucleotide, usually a synthetic polynucleotide, which is single stranded and selected in view of the known sequence of the target polynucleotide sequence. The polynucleotide primer is usually comprised of a sequence of at least 16 nucleotides, preferably, 24 to 90 nucleotides, more preferably, 24 to 64 nucleotides. The polynucleotide primer terminates at its 3' end in a 2 to 9, preferably, 4 to 8, nucleotide sequence (S1), which is complementary with the 3' ends of both of the complementary single stranded polynucleotide sequences. The polynucleotide primer has at least an 8, preferably, 12 to 45, more preferably, 12 to 36, nucleotide sequence (S2) that is 5' of, and preferably contiguous with, S1. Generally, S2 is 50 to 70%, preferably, 60% to 80%, complementary to both the nucleotide sequences contiguous with the 3' ends of the complementary single stranded polynucleotide sequences.

The primer may comprise modified bases such as phosporothiocates, methylated bases, phosphonates and the like. The primer may also comprise ribonucleotides although the nucleotide at the 3' end of the polynucleotide primer is usually a deoxynucleotide. The number of and nature of the nucleotides in the sequence of the polynucleotide primer hybridizable with the target polynucleotide sequences should be such that stringency conditions used to hybridize the polynucleotide primer to both of the complementary strands prevents excessive random non-specific hybridization.

The polynucleotide primer can contain at its 5' end nucleotides other than those in S2. These additional nucleotides can serve as ligands after extension and amplification of the extended primer and may, therefore, include sequences that bind to nucleic acid binding proteins, for example. The number of nucleotides other than those in S1 and S2 may vary widely, usually within the range of 0–2000, frequently 0–100, preferably 0–30.

It is also within the scope of the present invention to include one or more ambiguous nucleotides in S2 of the primer. The term "ambiguous nucleotide" means that the nucleotide is capable of binding to more than one of the nucleotides A, T, G and C. Exemplary of such ambiguous nucleotides is inosine. Ambiguous nucleotides are introduced to increase binding when S2 has a relatively low level of complimentarily with the nucleotide sequences contiguous with the 3' ends of single stranded polynucleotide sequences. However, excessive numbers of ambiguous nucleotides decrease specificity of binding and can lead to random priming. Preferably, S2 may contain 0 to 5 ambiguous nucleotides, more preferably, 0 to 3 ambiguous nucleotides.

In a more preferred embodiment, S1 of the primer is comprised of at least 75% of nucleotides guanosine (G) and cytidine (C). Preferably, S1 is comprised of at least 50% G and C. Series of G's and C's relatively uninterrupted by A's and T's are particularly useful because of their relatively tight binding to one another.

Deoxynucleoside triphosphates—deoxynucleosides having a 5'-triphosphate substituent. The deoxynucleosides are pentose sugar derivatives of nitrogenous bases of either purine or pyrimidine derivation, covalently bonded to the 1'-carbon of the pentose sugar. The purine bases include adenine(A), guanine(G), inosine, and derivatives and analogs thereof. The pyrimidine bases include cytosine (C), thymine (T), uracil (U), and derivatives and analogs thereof.

The derivatives and analogs include any substrate of a polydeoxynucleotide polymerase that can be incorporated into a polynucleotide through catalysis by such enzyme. The derivates and analogs are exemplified by those that are recognized and polymerized by the enzyme in a similar manner to the underivitized nucleoside triphosphates. Examples of such derivatives or analogs by way of illustration and not limitation are those that are modified with a reporter group, biotinylated, amine modified, radiolabeled, alkylated, and the like and also include phosphorothioate, phosphite, ring atom modified derivatives, unnatural bases, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

Polydeoxynucleotide polymerase —a catalyst, usually an enzyme, for forming an extension of the polynucleotide primer along a nucleic acid template. The polydeoxynucleotide polymerase is a template dependent polydeoxynucleotide polymerase and utilizes the deoxynucleoside triphosphates as building blocks for extending the 3' end of the polynucleotide primer to provide a sequence complementary with a single stranded polynucleotide sequence. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase (Vent is a trademark of New England BioLabs, Beverly, Mass.), Pfu DNA polymerase, Taq DNA polymerase, and the like, derived from any source such as cells, bacteria, for example, E. coli, plants, animals, virus, thermophilic bacteria, and so forth. Where the target polynucleotide sequence is RNA, reverse transcriptase is used as at least one of the polynucleotide polymerases to facilitate extension of the primer along the complementary strands of the polynucleotide analyte. Preferably the polynucleotide polymerase is stable at 95° C. and will usually be a thermophilic polymerase.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two polynucleotide sequences to hybridize with each other is based in a large part on the degree of complimentarily of the two polynucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Another factor to be considered is the nature of the nucleotide pairs that are opposite in the two strands. Some nucleotide pairs, such as G and C, have greater binding affinities for one another than do other pairs. Increased stringency is achieved by elevating the temperature, increasing the ratio of cosolvents, lowering the salt concentration, and the like.

Homologous or substantially identical—In general, two polynucleotide sequences that are identical, or at least can each hybridize to the same polynucleotide sequence, are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—two sequences are complementary when the sequence of one can bind to the sequence of the other in an anti-parallel sense wherein the 3' end of each sequence binds to the 5' end of the other sequence and, for example, among the natural bases each A, T(U), G, and C of one sequence is then aligned with a T(U), A, C, and G, respectively, of the other sequence.

Non-contiguous—two sequences are non-contiguous when there is at least one nucleotide, usually at least 10 nucleotides, between the two sequences.

Contiguous—sequences are considered to be contiguous when there are no nucleotides between the two sequences.

Copy—a sequence that is identical to or homologous with a single stranded polynucleotide sequence as differentiated from a sequence that is complementary to or hybridizable with the sequence of such single stranded polynucleotide. In single primer amplification described above in the background section, a complementary sequence of a single stranded polydeoxynucleotide sequence is produced initially as the result of the extension of a polynucleotide primer, and a sequence that is identical to or homologous with the single stranded polydeoxynucleotide sequence is subsequently obtained from further extension of the polynucleotide primer along the aforementioned complementary sequence.

Means for extending a primer—a polynucleotide polymerase, and may also include nucleoside triphosphates or analogs thereof capable of acting as substrates for the enzyme and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes", Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of the signal producing system. Usually the label or reporter group or molecule is conjugated to or becomes bound to a polynucleotide probe or a polynucleotide primer and is capable of being detected directly, or indirectly by being bound through a specific binding reaction, to a detectable substance. Labels able to be detected indirectly include polynucleotides such as a polynucleotide primer or a specific polynucleotide sequence that can act as a ligand for a complementary polynucleotide or provide a template for amplification or ligation or act as a ligand such as for a repressor protein; haptens; antibodies; receptors such as avidin; ligands such as biotin and the like. Labels able to be detected directly may be isotopic or nonisotopic, usually non-isotopic, and can be a catalyst, such as an enzyme, ribozyme, a substrate for a replicase such as QB replicase, promoter, dye, fluorescent molecule, chemiluminescer, coenzyme, enzyme substrate, radioactive group, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence. Methods for binding of labels to nucleotides are well-known and described, for example, by Engelhardt, et al., in European Patent Application Publication number 0 302 175.

Signal Producing System—The signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, such as detection of electromagnetic radiation, desirably by visual examination. The signal-producing system is described more fully in U.S. patent application Ser. No. 07/555,323, filed Jul. 19, 1990, the relevant disclosure of which is incorporated herein by reference.

Ancillary Materials—Various ancillary materials will frequently be employed in the method in accordance with the present invention. For example, buffers will normally be present in the medium, as well as stabilizers for the medium and the reaction components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above, one embodiment of a method in accordance with the present invention permits production of at least one copy of a pair of complementary single stranded polynucleotides. The method comprises forming, in the presence of nucleoside triphosphates and template dependent polynucleotide polymerase along each of the complementary single stranded polynucleotides, an extension of a polynucleotide primer. The polynucleotide primer is comprised of at least a sequence of 16 nucleotides terminating at its 3' end in a 2 to 9 nucleotide sequence (S1), which is complementary with the 3' ends of both of the complementary single stranded polynucleotides. The polynucleotide primer has at least an 8 nucleotide sequence (S2) that is 5' of S1, where S2 is 50 to 80% complementary to the nucleotide sequences contiguous with the 3' ends of the complementary single stranded polynucleotides. The extended polynucleotide primer and the single stranded polynucleotides are then dissociated.

This embodiment is depicted schematically in FIG. 1. The 3' end of polynucleotide primer P having sequence S1 hybridizes with the 3' end of each of complementary single stranded polynucleotide sequences T1 and T2, which are part of complementary single stranded target polynucleotide sequences M1 and M2. A sequence S2 located 5' of sequence S1 hybridizes with sequence C1, which is contiguous with T1 at the 3' end, and with sequence C2, which is contiguous with T2 at the 3' end. S1 is complementary with T1' at the 3' end of T1 and with T2' at the 3' end of C2. S2 has two sequences S2a and S2c complementary with sequences C1a and C1c, respectively, of single stranded polynucleotide sequence M1 and two sequences S2b and S2d complementary with sequences C2b and C2d, respectively, of single stranded polynucleotide sequence M2. In the presence of deoxynucleoside triphosphates and DNA polymerase and under appropriate reaction conditions, the polynucleotide primer P is extended along both M1 and M2 to produce extended primers EP1 and EP2. The extension of extended primer EP1 is complementary to M1 and the extension of extended primer EP2 is complementary to M2. After dissociation from their respective duplexes the products, ss polydeoxynucleotides EP1 and EP2, are obtained. Polynucleotide primer P hybridizes to EP1 and EP2. P hybridizes to EP1 by virtue of S1 hybridizing to T2' of EP1, which is also present in M2 and by virtue of S2 of P hybridizing to C2b and C2d of EP1, which are also present in M2. P hybridizes to EP2 by virtue of S1 hybridizing to T1' of EP2, where T1' is also present in M1, and by virtue of P hybridizing to C1a and C1c of EP2, which are also present in M1. Primer P is extended along EP1 and EP2 to give EP1' and EP2', which contain the sequences S1', S2a', S2b', S2c' and S2d', which are fully complementary to polynucleotide primer P. EP1' and EP2' are capable of forming stem-loop structures because each contains portions that are internally hybridizable when EP1' and EP2' are in single stranded form. Further repetition results in multiple copies of EP1' and EP2', which can be detected.

Figure 2:
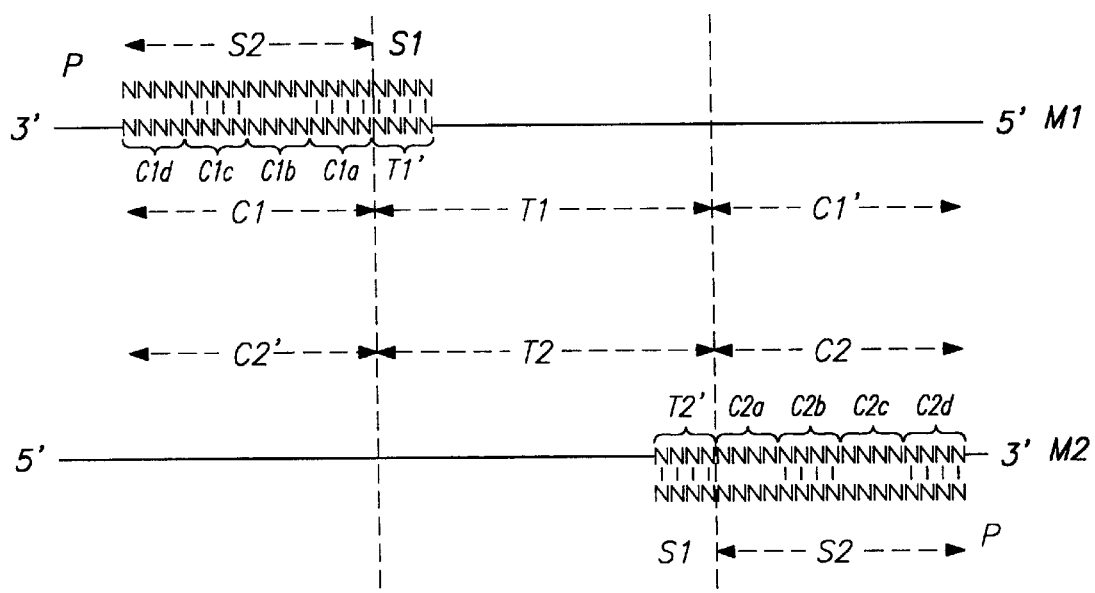
FIG. 2 is a schematic demonstrating construction of a primer for use in the present invention.

FIG. 2 depicts an example of the manner in which the selection of the polynucleotide primer is made. In FIG. 2 lines between nucleotides (N and N) in M1 and the primer P and in M2 and the primer P indicate that the nucleotides are complementary. Complementary single stranded target polynucleotide sequences M1 and M2 contain polynucleotide sequences T1 and T2, respectively, together with sequences that are contiguous with T1, namely C1 and C1', and with T2, namely C2 and C2'. As can be seen, M1 and M2 are chosen such that a single primer can be prepared wherein the first four nucleotides at the 3' end of the primer (S1) are complementary to the four nucleotides at the 3' end of T1 (T1') and the four nucleotides at the 3' end of T2 (T2'). S2 of the primer is then selected such that the first four nucleotides at the 3' end of S2 are complementary to the four nucleotides at the 5' end of C1 (C1a) but are not necessarily complementary to the four nucleotides at the 5' end of C2 (C2a). The next four nucleotides of S2 are complementary to the next four nucleotides of C2 (C2b) but not necessarily complementary to the next four nucleotides of C1 (C1b). The primer is completed by selecting the remaining eight nucleotides, where each quartet is alternately complementary to C1c of M1 and C2d of M2, respectively, such that the resulting primer has 20 nucleotides wherein there are five quartets of nucleotides. The quartet at the 3' end of the primer is complementary to the four nucleotides at the 3' end of T1 and T2, respectively. The remaining nucleotides of the primer are composed of a series of four quartets where the quartets are alternately complementary with C1 and C2. The quartets are taken in order corresponding to substantially complementary quartets at respectively ordered positions located alternately within sequences contiguous with the 3' ends of each of the complementary single stranded polynucleotide sequences.

It is generally within the scope of the invention to form the primer in a manner similar to that described above with multiplets of nucleotides in place of quartets wherein the multiplets each respectively may be two to six nucleotides, preferably, three to five nucleotides, and may be the same number or different number of nucleotides in each multiplet.

Furthermore, the present invention may be practiced without utilizing the ordered approach referred to above. In this situation the complementary versus non-complementary selection of nucleotides in S2 is made on a random basis such that sufficient hybridization of the primer to both of sequences contiguous to the 3' ends of the complementary single stranded polynucleotide sequences is obtained in order to achieve extension of the primer along both of the complementary single strand sequences. In general, S2 is at least 50%, usually 50 to 80%, preferably 60 to 80%, complementary with the nucleotide sequences contiguous with the 3' ends of the complementary single stranded polynucleotide sequences.

The methods of the invention have application in any situation where a polynucleotide sequence has known sequences contiguous with each end. The methods find particular use in single primer amplification, described above, wherein it is desired to form one or more copies of a target polynucleotide sequence.

When the present method is applied to replicating a target polynucleotide sequence, the following steps are repeated at least once: (a) the polynucleotide primer is caused to hybridize with and extend along the extended primers to form a second duplex comprising extended primers and (b) the extended primers are dissociated from the second duplex. In this manner a copy of a pair of complementary single stranded polynucleotides is obtained having bonded to each of its single stranded polynucleotides a sequence at each of the 3' ends that is identical to the polynucleotide primer and a sequence at each of the 5' ends that is complementary to the polynucleotide primer. Normally, this process is repeated at least three times. The method can comprise repetition of the above steps wherein the number of copies of the pair of single stranded polynucleotides is increased by at least a factor of a thousand up to that number of copies that is suitable for reliably detecting the target polynucleotide sequence.

The method has application where the target polynucleotide sequence is DNA or RNA.

In one aspect the polynucleotide primer is labeled with a reporter molecule. The reporter molecule can be, for example, a detectable group or a binder such as biotin or a nucleotide sequence other than the sequence that hybridizes with the sequence complementary to S2. The extended primer can be detected by means of a reporter molecule covalently bonded to a probe. In this approach the probe usually has a nucleotide sequence that is homologous or complementary to a portion of the target nucleotide sequence.

In accordance with the above another embodiment of the invention is a method for producing multiple copies of a polynucleotide sequence and its complement. The method comprises providing in combination (1) a pair of complementary single stranded polynucleotides having the polynucleotide sequence and its complement, (2) a single polynucleotide primer being comprised of at least a sequence of 16 nucleotides terminating at its 3' end in a 2 to 9 nucleotide sequence (S1), which is complementary with the 3' ends of both the polynucleotide sequence and its complement, wherein the polynucleotide primer has a specifically designed sequence of at least 8 nucleotides (S2) that is 5' of S1, wherein S2 is 50 to 80% complementary to each of the nucleotide sequences contiguous with the 3' ends of the polynucleotide sequence and its complement, (3) nucleoside triphosphates, (4) template dependent polynucleotide polymerase. The combination is incubated under conditions for either wholly or partially sequentially or concomitantly (1) dissociating the polynucleotide sequence and its complement, (2) hybridizing the polynucleotide primer with the sequence at the 3' end of the polynucleotide sequence and its complement, (3) extending the polynucleotide primer along the polynucleotide sequence and its complement to provide a first complementary pair of extended polynucleotide primers, (4) dissociating the first complementary pair of extended polynucleotide primers from the polynucleotide sequence and its complement, (5) hybridizing single stranded extended polynucleotide primers from the first complementary pair with the polynucleotide primer, (6) extending the polynucleotide primer along the single stranded extended polynucleotide primers to provide a second complementary pair of extended polynucleotide primers, (7) dissociating the second complementary pair of extended polynucleotide primers from the first complementary pair of extended polynucleotide primers, and (8) repeating steps (5)–(7) above.

Another embodiment of the invention is a method for determining the presence of a polynucleotide analyte in a sample suspected of containing the analyte. The analyte has complementary single stranded polynucleotide sequences that, together with nucleotide sequences contiguous with the 3' ends of the complementary single stranded polynucleotide sequences, are at least partially known. In the method a combination is provided comprising (1) the sample, (2) a polynucleotide primer comprised of at least a sequence of 16 nucleotides terminating at its 3' end in a 2 to 9 nucleotide sequence (S1), which is complementary with the 3' ends of both of the complementary single stranded polynucleotide sequences, wherein the polynucleotide primer has a specifically designed sequence of at least 8 nucleotides (S2) that is 5' of S1, wherein S2 is 50 to 80% complementary to each of the nucleotide sequences contiguous with the 3' ends of the complementary single stranded polynucleotide sequences, (3) nucleoside triphosphates and (4) template dependent polynucleotide polymerase. The combination is incubated under conditions for either wholly or partially sequentially or concomitantly (1) dissociating complementary sequences of the analyte into single stranded polynucleotides, (2) hybridizing the polynucleotide primer with the 3' end of the single stranded polynucleotide sequences, (3) extending the polynucleotide primer along the single stranded polynucleotide sequences to provide a first complementary pair of extended polynucleotide primers, (4) dissociating said first complementary pair of extended polynucleotide primers from the single stranded polynucleotide sequences, (5) hybridizing single stranded extended polynucleotide primers from the first complementary pair with the polynucleotide primer, (6) extending the polynucleotide primer along the single stranded extended polynucleotide primers to provide a second complementary pair of extended polynucleotide primers, (7) dissociating the second complementary pair of extended polynucleotide primers from the single stranded extended polynucleotide primers, and (8) repeating steps (5)–(7) above. Steps (a) and (b) are performed wholly or partially sequentially or concomitantly. An examination for the presence of extended polynucleotide primers is conducted, the presence thereof indicating the presence of the polynucleotide analyte. Steps (3)–(5) are repeated a least 1 time, preferably, at least 10 times; usually it is preferable that the number of repetitions be less than 60. Generally, steps (3)–(5) are repeated a number of times sufficient to provide an accurate detection of the polynucleotide analyte. Where the polynucleotide analyte is RNA, it can first be converted to DNA by means of a primer and reverse transcriptase, or the polydeoxynucleotide polymerase used in at least step B can be reverse transcriptase.

Appropriate reaction conditions are chosen for carrying out the methods in accordance with the present invention. The following description sets forth such appropriate conditions, which are subject to modification by those skilled in the art depending on the specific reagents and other molecules chosen for any particular application.

Generally, an aqueous medium is employed. Other polar cosolvents may also be employed in the medium, usually oxygenated organic solvents of from 1–6, more usually from 1–4, carbon atoms, including alcohols, ethers and the like. Usually, these cosolvents are present in less than about 70 weight percent, more usually, in less than about 30 weight percent.

The pH for the medium is usually in the range of about 5.5 to 10, more usually, in the range of about 6.5–9.5, and, preferably, in the range of about 7–9. The pH and temperature are chosen and varied, as the case may be, so as to cause, either simultaneously or wholly or partially sequentially, dissociation of any internally hybridized sequences, hybridization of the primer with the single stranded polynucleotide sequences and extended primer once the primer has been extended, extension of the primer along the single stranded polynucleotide sequences and extended primer, and dissociation of the extended primer from its duplex. In some instances, a compromise will be made in optimizing the speed, efficiency, and specificity of these steps depending on whether it is desired to perform the above steps wholly or partially sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method. As mentioned above, appropriate reaction conditions are chosen in order to achieve extension of the primer along the single stranded polynucleotide sequences. These reaction conditions are dependent on a number of considerations such as, for example, the salt concentration and the pH of the medium, the solvent composition of the medium used, the length of the target polynucleotide sequence and the length and nucleotide composition of sequences S1 and S2 of the primer. The temperature for extension of the primer depends on the activity of the polymerase and can range from 20° to 95° C., usually 35° to 90° C., frequently 50° to 80° C. The first one or two cycles in a method in accordance with the present invention may be conducted at a different, usually lower temperature than subsequent cycles, usually no more than 15° different, preferably less than 10° different. The dissociation or melting step temperature usually is 45° to 100°, more usually 70° to 98° C. The hybridization step temperature is usually 25° to 80° C., more usually 35° to 70° C.

Normally, in conducting the method of the invention for amplification of nucleic acids, the medium is cycled between two or three temperatures. The melting temperatures for the present method in conjunction with amplification generally ranges from 85–100° C., the hydridization temperature from about 40–80° C., and the primer extension temperature from about 55–85° C.

The present method is conducted for a time sufficient to achieve a desired number of copies of the extended primer or a sequence complementary thereto. This, in turn, depends on the purpose for which the amplification is conducted, such as, for example, an assay for a polynucleotide analyte. Generally, the time period for conducting the method is from about 20 seconds to 10 minutes per cycle and any number of cycles can be used from 1 to as high as 80 or more, usually 5 to 60, frequently 10–50. As a matter of convenience it is usually desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer. Generally, the time period for conducting the method is from about 5 to 200 minutes.

The amount of the target polynucleotide sequence can be as low as one or two molecules in a sample but generally varies from about $10^2$ to $10^{14}$, more usually from about $10^3$ to $10^8$ molecules in sample volumes that may be less than a microliter but will usually be 1–1000 $\mu$L, more usually 5–250 $\mu$L. The amount of the polynucleotide primer should be at least as great as the number of copies desired and is usually present in at least $10^{-9}$ M, preferably $10^{-7}$ M, and more preferably at least about $10^{-6}$ M. Preferably, the concentration of the polynucleotide primer is substantially in excess over, preferably at least 100 times greater than, the concentration of the single stranded polynucleotide.

The concentration of the deoxynucleoside triphosphates in the medium can vary widely; preferably, these reagents are present in an excess amount. The deoxynucleoside triphosphates are usually present in $10^{-6}$ to $10^{-2}$ M, preferably $10^{-5}$ to $10^{-3}$ M.

The concentration of the template-dependent polynucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The order of combining of the various reagents to form the combination may vary. Generally, the single stranded polynucleotide sequences are obtained from genetic material, DNA or RNA, from an organism or cell. Generally complementary single stranded polynucleotide sequences and the primer are combined with a pre-prepared combination of deoxynucleoside triphosphates, and template-dependent polydeoxynucleotide polymerase. However, simultaneous addition of all of the above, as well as other step-wise or sequential orders of addition, may be employed.

The concentration and order of addition of reagents and conditions for the method are governed generally by the desire to maximize the number of copies of the extended primer and the rate at which such copies are formed and the fidelity of replication. Generally, it is desirable to increase the number of copies of the extended primer by at least a factor of $10^2$, preferably a factor of $10^4$, more preferably $10^6$ or more.

In carrying out the method of the invention as applied to the detection of a polynucleotide analyte, the considerations as to media, pH, temperature, and times are as described above. While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amplification method. The primary consideration is that a sufficient number of copies of extended primer be produced in relation to the polynucleotide analyte so that such copies can be readily detected and provide an accurate determination of the polynucleotide analyte if present.

The copies of extended primer can be detected in numerous ways. For example, in the present method, an oligonucleotide complementary with the single stranded polynucleotide sequence and optionally the polynucleotide primer can be labeled with a reporter molecule such as a ligand, a small organic molecule including fluorescers, chemiluminescers and the like, catalysts, co-enzymes, radioactive substances, amplifiable polynucleotide sequences, a polypeptide, a support, an operator or the like. The labeled oligonucleotide may be added after the final primer extension and caused to hybridize with one of the single stranded polynucleotide sequences; and the signal from the label may then be measured with or without separating the hybridized oligonucleotide from the rest of the medium. Examples of particular labels or reporter molecules and their detection can be found in U.S. patent application Ser. No. 07/555,323 filed Jul. 19, 1990, the relevant disclosure of which is incorporated herein by reference. Other assay formats and detection formats are disclosed in U.S. patent applications Ser. Nos. 07/229,282 and 07/399,795 filed Jan. 19, 1989, and Aug. 29, 1989, respectively, U.S. patent application Ser. No. 07/555,323 filed Jul. 19, 1990, U.S. patent application Ser. No. 07/555,968 filed Jul. 19, 1990, U.S. patent application Ser. No. 07/776,538 filed Oct. 11, 1991, U.S. patent application Ser. No. 07/923,079 filed Jul. 31, 1992, all of which have been incorporated herein by reference. Any standard method for specifically detecting nucleic acid sequences can be used.

One method for detecting nucleic acids is to employ nucleic acid probes. One method utilizing such probes is described in U.S. Pat. No. 4,868,104, the disclosure of which is incorporated herein by reference.

Detection of the signal depends upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Various techniques can be employed for preparing the polynucleotide primer used in the present method after the nucleotide composition of such primer has been determined as described above. Such sequences can be obtained by biological synthesis or by chemical synthesis. For short sequences (up to about 100 nucleotides) chemical synthesis is frequently more economical as compared to biological synthesis. In addition to economy, chemical synthesis provides a convenient way of incorporating low molecular weight compounds and/or modified nucleotides or bases during the synthesis step. Furthermore, chemical synthesis is very flexible in the choice of length of the primer. The polynucleotide primer can be synthesized by standard methods such as those used in commercial automated nucleic acid synthesizers. Chemical synthesis of DNA or RNA on a suitably modified glass or resin can result in DNA or RNA covalently attached to the surface. This offers advantages in washing and sample handling. For longer sequences standard replication methods employed in molecular biology can be used such as the use of M13 for single stranded DNA as described by J. Messing, *Methods Enzymol* (1983) 101: 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol* (1979) 68: 90) and synthesis on a support (Beaucage, et al., *Tetrahedron* (1981) *Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

The polynucleotide primer may contain at least one phosphorothioate diester and can be prepared according to known techniques. Oligonucleotide synthesis can be carried out as described above up to the point where introduction of the phosphorothioate diester is desired. The phosphorothioate diester can be introduced in a number of ways such as, for example, oxidations utilizing a thiolating reagent such as a diacyldisulfide or tetraethyl thiuram disulfide, which are commercially available. The remaining nucleotides are then introduced. Other methods of preparing phosphorothioate containing polynucleotides are described in WO9008838, WO8911486, U.S. Pat. No. 4,910,300, EP318245, the relevant disclosures of which are incorporated herein by reference. Other methods of preparing a phosphorothioate containing polynucleotide are described by (a) Yau, et al., *Tetrahedron Lett.* (1990)31(14): 1953–1956; (b) Brill, et al., ibid. (1989) 30(48):6621–6624; (c) Caruthers, et al., *Nucleic Acids Symp. Ser.* (1989)21: 119–120; (d) Caruthers, et al., *Nucleosides Nucleotides* (1988)8(5–6): 1011–1014; (e) Brill, et al., *J. Am. Chem. Soc.* (1989)111(6): 2321–2322.

As a matter of convenience, predetermined amounts of reagents employed in the present invention are provided in a kit in packaged combination. The kits can be used in accordance with the methods of the present invention in determining a polynucleotide analyte, where the analyte has complementary single stranded polynucleotide sequences, the 3' ends of which being at least partially known and characteristic for the analyte or can be identified. The kit comprises in packaged combination: (a) a polynucleotide primer comprised of at least a sequence of 16 nucleotides terminating at its 3' end in a 2 to 9 nucleotide sequence (S1), which is complementary with the 3' ends of both of the complementary single stranded polynucleotide sequences, wherein the polynucleotide primer has at least an 8 nucleotide sequence (S2) that is 5' of S1, S2 being 50 to 80% complementary to the nucleotide sequences contiguous with the 3' ends of the complementary single stranded polynucleotide sequences; (b) nucleoside triphosphates and (c) template dependent polynucleotide polymerase.

The kit can further include a labeled or unlabeled polynucleotide probe capable of binding to extended primer produced in the method of the invention. The kits above can further include in the packaged combination deoxynucleoside triphosphates (dNTPs) such as, e.g., deoxyadenosine triphosphate (dATP), deoxyguanosine triphosphate (dGTP), deoxycytidine triphosphate (dCTP) and deoxythymidine triphosphate (dTTP) or derivatives or analogs of the above. The kit can further include a polydeoxynucleotide polymerase and members of a signal producing system and also various buffered media, some of which may contain one or more of the above reagents.

The relative amounts of the various reagents in the kits can be varied widely to provide for concentrations of the reagents that substantially optimize the reactions that need to occur during the present method and to further substantially optimize the sensitivity of any assay, in which the present method is employed. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit.

EXAMPLES

The invention is demonstrated further by the following illustrative examples. Temperatures are in degrees centigrade (°C.) and parts and percentages are by weight unless otherwise indicated.

Example 1

Amplification of Regions of M13 mp18 DNA
Primers

Primer 1: 5' CTC-GCT-TGA-AAA-GAG-TAT-ATG-GCC-AGT-CTT-GCG-GG 3' (SEQ ID NO:1)
Primer 2: 5' CTC-GCT-TTA-AAA-TGA-GAT-ATT-TTC-AGT-CAA-ACG-GG 3' (SEQ ID NO:2)
Primer 3: 5' ACG-CGA-ATC-AGT-TAA-AAC-ATT-CAT-CAT-TGA-CC-CC 3' (SEQ ID NO:3)
Primer 4: GAT-AGAR-GCA-ACA-CAT-TCA-TAA 3' (SEQ ID NO:4)
Primer 5: GAT-TCA-GCA-ATT-AAG-CTC-TAA-GCC 3' (SEQ ID NO:5)

Primer 1 has 22 complementary bases in the region bases number 335 to 369 of M13 mp18 DNA and 22 complementary bases in the region bases number 1384 to 1418.

Primer 2 has 26 complementary bases in region bases number 335 to 369 of M13 mp18 DNA and 24 complementary bases in the region bases number 1278 to 1312.

Primer 3 has 25 complementary bases in the region bases number 527 to 561 of M13 mp18 DNA and 24 complementary bases in the region bases number 1194 to 1228.

Primer 4 hybridizes has 21 complementary bases in the region bases number 630–650 of M13 mp18 DNA.

Primer 5 has 24 complementary bases in the region bases number 216–239 of M13 mp18 DNA.

Conditions for Amplification

Each of primers 1–3 were incubated with varying amounts of target M13 mp18 RF and temperature cycled with TAQ DNA polymerase (Perkin Elmer/Cetus). Specifically, 1 µM of primer was mixed with $6 \times 10^{10}$, $6 \times 10^7$, $6 \times 10^4$ or 60 M13 mp18 target molecules (hereinafter "targets") in 1×buffer (10 mM TRIS-HCl, pH 8.3, 50 mM KCl, 1.5 mM MgCl$_2$, 0.0001% gelatin) in a volume of 100 microliters with 200 µM, respectively, dATP, dGTP, dCTP, dTTP. 2.5 units of TAQ polymerase were added and temperature cycling was conducted as follows: 10 cycles each of 94° C., 1 min., 34° C., 2 min., 72° C., 3 min., were followed by 30 cycles each of 94° C., 1 min., 58° C., 2 min, 72° C., 3 min.

15 microliter aliquots of the above reaction mixtures were subjected to electrophoreses on a 1.2% agarose gel containing 90 mM TRIS-Borate, 1 mM EDTA buffer (pH 8.3) and 0.5 microgram/ml ethidium bromide (Maniatis, T. et. al, *Molecular Cloning,* Cold Spring Harbor, 1982, pp 153–162), and visualized by ultraviolet illumination.

As positive controls, PCR was performed using Primer 1 plus Primer 4 in one control, both at 0.5 $\mu$M final concentration; Primer 3 plus Primer 5 in another control also both at 0.5 $\mu$M final concentration; and Primer 4 plus Primer 5 in another control, each at 0.5 $\mu$M. The amplification was conducted under the above conditions using $6\times10^{10}$ M13 mp18 targets. The PCR primer pair of Primer 1 and Primer 4 was expected to produce a 316 bp amplicon. The PCR primer pair of Primer 3 and Primer 5 was expected to produce a 979 bp amplicon. The PCR primer pair of Primer 4 plus Primer 5 was expected to produce an amplicon of 435 base pairs.

Results

Figure 3:
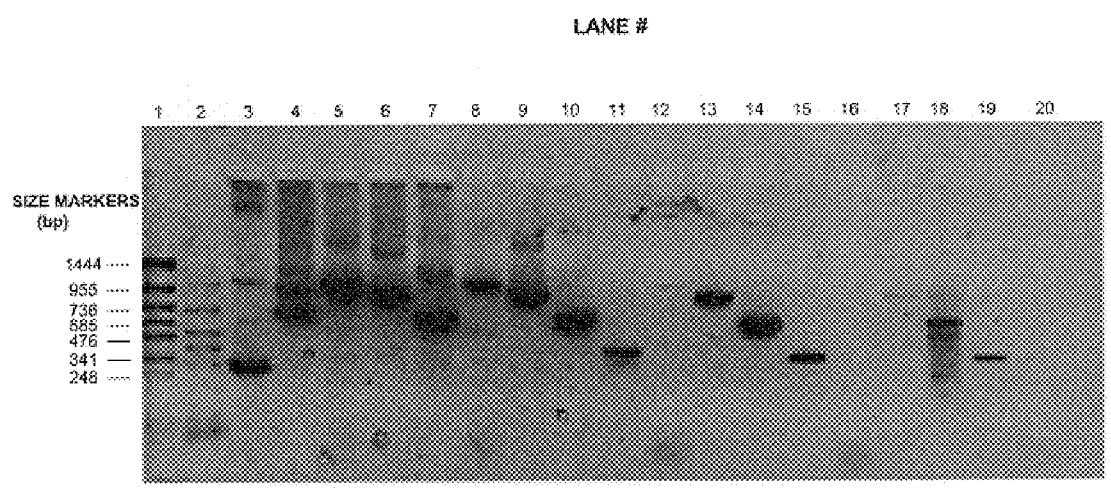
FIG. 3 is a depiction of the results of the electrophoresis of aliquots of the reaction mixtures of Example 1 on agarose gels.

Primers 1, 2 and 3 were each designed to hybridize, with some mismatches, to two regions of the M13 mp18 replicative form double stranded DNA. FIG. 3 summarizes the results of the above reactions. See the legend of FIG. 3 for the description of the reactions represented in each lane, the expected size of the amplicon and the number of targets amplified where appropriate. Aliquots of each reaction mixture were subjected to agarose gel electrophoreses with ethidum bromide staining.

All primers, including primer pairs used for PCR, gave rise to the expected size DNA amplicons. In some reactions nonspecific amplicons were present in the lanes as well. Single primer amplification using Primers 2 and 3, respectively, generated the appropriate amplicons even with as few as 60 DNA targets. Amplicon identification was confirmed by restriction digestion and Southern blotting to appropriate probes.

It is interesting to note the results when Primer 3, which alone can generate an amplicon by single primer amplification, was mixed with Primer 5. Primer 3 and Primer 5 mixed together can, in principle, result in a PCR amplicon. The single primer product from composite Primer 3 was generated in this reaction, namely, a 701 bp amplicon, as well as the PCR product derived from both primers together, namely, a 979 bp amplicon. The smaller single primer product from Primer 3 above, 701 bp, dominated the amplicon products of this reaction. The 701 bp amplicon had a much higher staining intensity than the 979 bp PCR amplicon. Hence, a single prime amplification will be produced even in an environment where PCR products can form. The SPA product may be favored in this specific reaction due to its shorter length.

FIG. 3 Legend

| Lane | Reaction |
|---|---|
| 1 | Control, DNA size standards (Stratagene, pUC19, Taq 1, Sau 3A1). |
| 2 | Control, DNA size standard (Research Genetics; 1000, 700, 500, 400, 300, 200, 100, 50 bp). |
| 3 | Primer 4 plus Primer 1, PCR positive control, 316 bp amplicon, $6 \times 10^{10}$ targets used. |
| 4 | Primer 3 plus Primer 5, PCR positive control, 701, 979 bp amplicons, $6 \times 10^{10}$ targets used. |
| 5 | Primer 1, 1084 bp amplicon, $6 \times 10^{10}$ targets used. |
| 6 | Primer 2, 978 bp amplicon, $6 \times 10^{10}$ targets used. |
| 7 | Primer 3, 701 bp amplicon, $6 \times 10^{10}$ targets used. |
| 8 | Primer 1, 1084 bp amplicon, $6 \times 10^{7}$ targets used. |
| 9 | Primer 2, 978 bp amplicon, $6 \times 10^{7}$ targets used. |
| 10 | Primer 3, 701 bp amplicon, $6 \times 10^{7}$ targets used. |
| 11 | Primer 4 plus Primer 5, PCR positive control, 435 bp amplicon, $6 \times 10^{7}$ targets used. |
| 12 | Primer 1, barely visible band at 1084 bp, $6 \times 10^{4}$ targets used. |
| 13 | Primer 2, 978 bp amplicon, $6 \times 10^{4}$ targets used. |
| 14 | Primer 3, 701 bp amplicon, $6 \times 10^{4}$ targets used. |
| 15 | Primer 4 plus Primer 5, PCR positive control, 435 bp amplicon, $6 \times 10^{4}$ targets used. |
| 16 | Primer 1, no amplicon visible, 60 targets used. |
| 17 | Primer 2, 978 bp amplicon barely visible, 60 targets used. |
| 18 | Primer 3, 701 bp amplicon with some smeary background, 60 targets used. |
| 19 | Primer 4 plus Primer 5, PCR positive control, 435 bp amplicon, 60 targets used. |
| 20 | Primer 4 plus Primer 5, no targets, negative control. |

Example 2

Amplification of Regions of *E. coli* Genomic DNA Primers

Primer 6: 5' TAC-AGT-TCC-TCG-TCA-GTC-TTA-ACA-GCA-CCC-GAT-TT 3' (SEQ ID NO:6)

Primer 7: 5' TTA-CAT-TTT-CTC-GCG-TAT-CTG-CAA-CGC-ACT-GTA-TT 3" (SEQ ID NO: 7)

Primer 6 has 24 complementary bases in the region bases number 858–892 of *E. coli* genomic DNA in the heat shock gene "J" and 25 complementary base pairs in the region bases number 1295–1329.

Primer 7 has 22 complementary base pairs in the region bases number 885–919 of *E. coli* genomic DNA in the heat shock gene "J" and 28 complementary bases in the region bases number 1296–1331.

The primers were designed to each hybridize to two separate sites on the *E. coli* genome. Each primer can form a number of base pairs at each of its two hybridization sites in Gene "J". Amplification of the region of DNA between these two priming sites using only one or the other primer species was demonstrated.

Conditions for Amplification

Primer 6 or Primer 7 was incubated with approximately 1000 *E. coli* target genomes in an amplification reaction. Primer concentration was varied between 0.5, 1.0, and 2.0 $\mu$M final concentration in the 100 $\mu$l reaction. Specifically, primer plus target was mixed with 1xbuffer (10 mM KCl, 10 mM $(NH_4)_2$ $SO_{41}$ 20 mM TRIS-HCl (pH 8.8), 2 mM Mg $SO_4$, 0.1% from Triton x-100 from New England Biolabs.), and 250 $\mu$M each DATP, dGTP, dCTP, dTTP. 2 units of Vent exo$^-_n$ DNA polymerase (New England Biolabs) was added last. Reaction mixtures were heated to 95° C. for 4 minutes, then cycled 60 times through a three temperature regimen of 92° C. for 30 seconds, 51° C. for 1 min. and 72° C. for 90 seconds. 10 $\mu$l aliquots of the cycled reaction mixtures were mixed with gel dyes and electrophoresed in 1.2% Agarose buffered by 90 mM TRIS-Borate, 1 mM EDTA, pH 8.3. Agarose gels were stained with 0.5 $\mu$g/ml Ethidium Bromide and visualized by ultraviolet illumination.

Results

Figure 4:
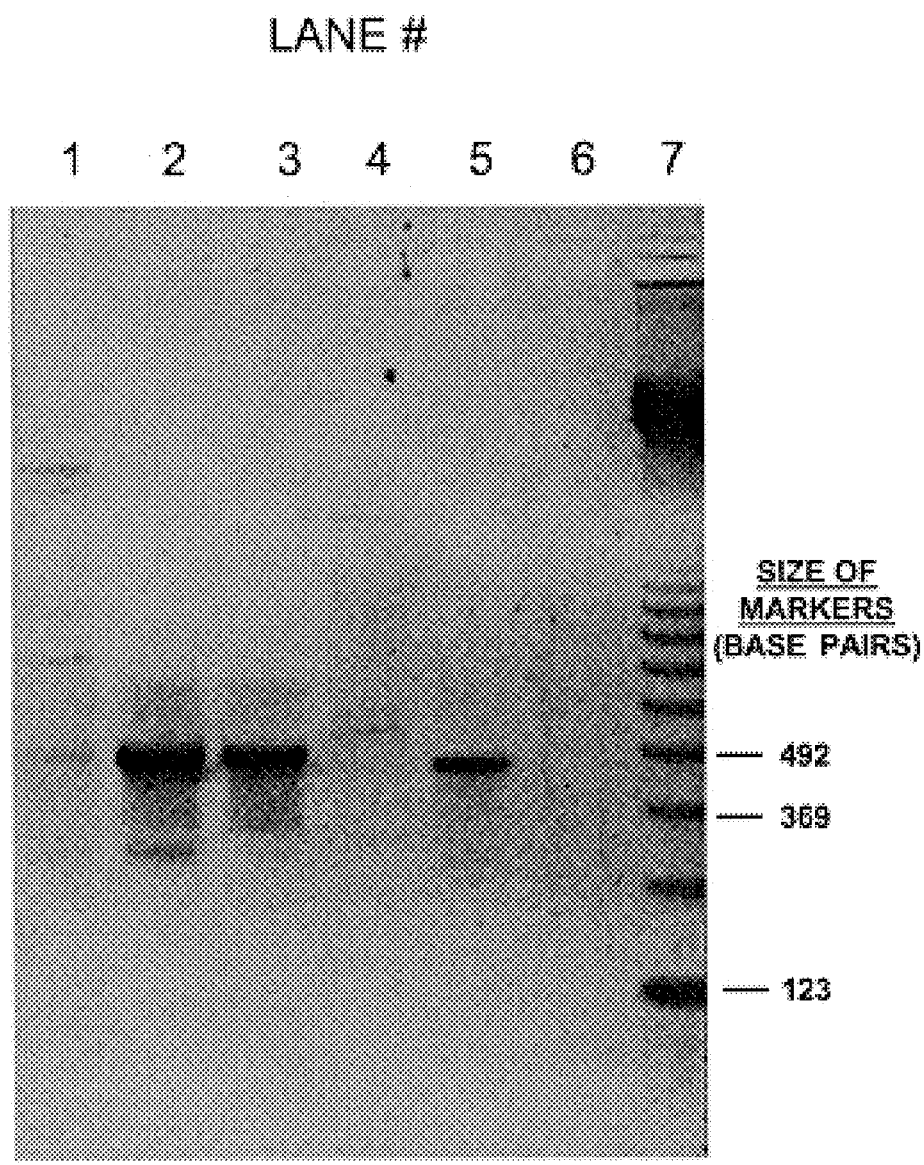
FIG. 4 is a depiction of the results of the electrophoresis of aliquots of the reaction mixtures of Example 2 on agarose gels.

FIG. 4 shows amplicon bands resulting from amplifications using each of the above primers. See the legend for FIG. 4 for the description of the reactions represented in each of the lanes, the concentration of the primer, the size of the amplicon obtained, and the number of targets amplified. Amplicon from Primer 6 was expected to be 472 base pairs. Amplicon from Primer 7 was expected to be 447 base pairs. The expected amplicons were indeed present in lanes 2, 3 and 5 of FIG. 4.

The identity of these amplicons was confirmed by restriction digestion and probe hybridization to the blotted amplicon DNA. It was demonstrated that single primer amplification was obtained by primers of a design shown above. Both 1.0 and 2.0 µM Primer 6 supported a specific amplification to produce the expected amplicon. 1.0 µM Primer 7 also resulted in a specific amplification of the expected amplicon.

FIG. 4 Legend

| Lane | Reaction |
|------|----------|
| 1 | Primer 6 at 0.5 µM, 472 bp amplicon, 1000 targets used. |
| 2 | Primer 6 at 1.0 µM, 472 bp amplicon, 1000 targets used. |
| 3 | Primer 6 at 2.0 µM, 472 bp amplicon, 1000 targets used. |
| 4 | Primer 7 at 0.5 µM, 447 bp amplicon, 1000 targets used. |
| 5 | Primer 7 at 1.0 µM, 447 bp amplicon, 1000 targets used. |

-continued

| Lane | Reaction |
|------|----------|
| 6 | Primer 7 at 2.0 µM, 447 bp amplicon, 1000 targets used. |
| 7 | 123 base pair size marker (Bethesda Research Labs) |

The above discussion includes certain theories as to mechanisms involved in the present invention. These theories should not be construed to limit the present invention in any way, since it has been demonstrated that the present invention achieves the results described.

The above description and examples disclose the invention including certain preferred embodiments thereof. Modifications of the methods described that are obvious to those of ordinary skill in the art such as molecular biology and related sciences are intended to be within the scope of the following claims and included within the metes and bounds of the invention.

What is claimed is:

1. A method of producing at least one copy of a pair of complementary single stranded polynucleotide sequences, said method comprising:
   (a) forming in the presence of nucleoside triphosphates and template dependent polynucleotide polymerase along each of said complementary single stranded polynucleotide sequences, an extension of a single polynucleotide primer, said polynucleotide primer being comprised of at least a sequence of 16 nucleotides terminating at its 3' end in a 4 to 8 nucleotide sequence (S1) that is complementary with the 3' ends of both of said complementary single stranded polynucleotide sequences, wherein said polynucleotide primer has a specifically designed sequence of at least 8 nucleotides (S2) that is 5' of said S1, said S2 being 50 to 80% complementary to each of the nucleotide sequences contiguous with the 3' ends of said complementary single stranded polynucleotide sequences, and
   (b) dissociating said extended polynucleotide primer and said single stranded polynucleotides thereby producing said copy of said single stranded polynucleotide sequences.

2. The method of claim 1 wherein said S2 is at least 60% complementary with each of said nucleotide sequences contiguous with the 3' ends of said complementary single stranded polynucleotide sequences.

3. The method of claim 1 wherein said pair of single stranded polynucleotide sequences and said copy are DNA.

4. The method of claim 1 wherein said polynucleotide primer is 24 to 90 nucleotides in length.

5. The method of claim 1 wherein said S2 contains at least one ambiguous nucleotide capable of binding to A, T, G and C.

6. The method of claim 5 wherein said ambiguous nucleotide is inosine.

7. The method of claim 1 wherein said S1 is at least 75% G and C.

8. The method of claim 1 wherein said S2 comprises a series of multiplets of nucleotides, said multiplets taken in order corresponding to at least 50% complementary multiplets at respectively ordered positions located alternately within sequences contiguous with the 3' ends of each of said complementary single stranded polynucleotide sequences.

9. The method of claim 8 wherein said S2 consists solely of said multiplets.

10. The method of claim 8 wherein said multiplets are quartets.

11. The method of claim 1 wherein said template-dependent polynucleotide polymerase is a DNA polymerase and said nucleoside triphosphates are dATP, dGTP, dCTP, and dTTP.

12. The method of claim 1 wherein said method is carried out at at least a 100-fold excess concentration of said polynucleotide primer relative to the concentration of said single stranded polynucleotides.

13. A method comprising repetition of the steps of claim 1 wherein said copy of said pair of complementary single stranded polynucleotide sequences has bonded to each of its 3' ends a sequence that is identical to said sequence S2 and a sequence at each of the 5' ends that is complementary to said sequence S2.

14. A method comprising repetition of the steps of claim 1 wherein the number of copies of said pair of single stranded polynucleotide sequences is increased by at least a factor of a thousand.

15. A method of producing multiple copies of a polynucleotide sequence and its complement, which comprises:
   (a) providing in combination (1) a pair of complementary single stranded polynucleotides having said polynucleotide sequence and its complement, (2) a single polynucleotide primer being comprised of a sequence of 24 to 90 nucleotides terminating at its 3' end in a 2 to 9 nucleotide sequence (S1) that is complementary with the 3' ends of both of said polynucleotide sequences and its complement, wherein said polynucleotide primer has a specifically designed sequence of at least 8 nucleotides (S2) that is 5' of said S1, said S2 being 50 to 80% complementary to each of the nucleotide sequences contiguous with the 3' ends of said polynucleotide sequence and its complement, (3) nucleoside triphosphates, (4) template dependent polynucleotide polymerase and (b) incubating said combination under conditions for either wholly or partially sequentially or concomitantly (1) dissociating said polynucleotide sequence and its complement, (2) hybridizing said polynucleotide primer with the sequences at the 3' end of said polynucleotide sequence and its complement, (3) extending said polynucleotide primer along said polynucleotide sequence and its complement to provide a first complementary pair of extended polynucleotide primers, (4) dissociating said first complementary pair of extended polynucleotide primers from said polynucleotide sequence and its complement, (5) hybridizing single stranded extended polynucleotide primers from said first complementary pair with said polynucleotide primer, (6) extending said polynucleotide primer along said single stranded extended polynucleotide primers to provide a second complementary pair of extended polynucleotide primers, (7) dissociating said second complementary pair of extended polynucleotide primers from said first complementary pair of extended polynucleotide primers, and (8) repeating steps (5)–(7) above thereby producing multiple copies of said polynucleotide sequences.

16. The method of claim 15 wherein said S1 is 4 to 8 nucleotides in length.

17. The method of claim 15 wherein said S2 is at least 60% complementary with each of said nucleotide sequences contiguous with the 3' ends of said polynucleotide sequence and its complement.

18. The method of claim 15 wherein said polynucleotide sequence or its complement or said first or second extended polynucleotide primer is DNA.

19. The method of claim 15 wherein said S2 contains at least one ambiguous nucleotide capable of binding to A, T, G and C.

20. The method of claim 19 wherein said ambiguous nucleotide is inosine.

21. The method of claim 15 wherein said S2 contains 1 to 4 ambiguous nucleotides capable of binding to A, T, G and C.

22. The method of claim 15 wherein said S1 is at least 75% G and C.

23. The method of claim 15 wherein said S2 comprises a series of multiplets of nucleotides, said multiplets taken in order corresponding to at least 50% complementary multiplets at respectively ordered positions located alternately within sequences contiguous with the 3' ends of each of said complementary single stranded polynucleotides.

24. The method of claim 23 wherein said S2 consists solely of said multiplets.

25. The method of claim 23 wherein said multiplets are quartets.

26. The method of claim 15 wherein said template-dependent polynucleotide polymerase is a DNA polymerase and said nucleoside triphosphates are dATP, dGTP, dCTP, and dTTP.

27. The method of claim 15 wherein said method is carried out at at least a 100-fold excess concentration of said polynucleotide primer relative to the concentration of said polynucleotide sequence and its complement.

28. A method comprising repetition of the steps of claim 15 wherein extended polynucleotide primer has an inverted repeat wherein one of the sequences of the inverted repeat is identical to the polynucleotide primer.

29. A method comprising repetition of the steps (5)–(7) of claim 15 wherein the number of said copies of said polynucleotide sequence and its complement is increased by at least a factor of a thousand.

30. A method for determining the presence of a polynucleotide analyte in a sample suspected of containing said analyte, said analyte having complementary single stranded polynucleotide sequences and nucleotide sequences contiguous with the 3' ends of said complementary single stranded polynucleotide sequences, said method comprising the steps of:

(a) providing in combination (1) said sample, (2) a polynucleotide primer comprised of at least a sequence of 16 nucleotides terminating at its 3' end in a 4 to 8 nucleotide sequence (S1) that is complementary with the 3' ends of both of said complementary single stranded polynucleotide sequences, wherein said polynucleotide primer has a specifically designed sequence of at least 8 nucleotides (S2) that is 5' of said S1, said S2 being 50 to 80% complementary to each of the nucleotide sequences contiguous with the 3' ends of said complementary single stranded polynucleotide sequences, (3) nucleoside triphosphates and (4) template dependent polynucleotide polymerase;

(b) incubating said combination under conditions for either wholly or partially sequentially or concomitantly (1) dissociating complementary sequences of said analyte into single stranded polynucleotides, (2) hybridizing said polynucleotide primer with the 3' end of said single stranded polynucleotide sequences, (3) extending said polynucleotide primer along said single stranded polynucleotide sequences to provide a first complementary pair of extended polynucleotide primers, (4) dissociating said first complementary pair of extended polynucleotide primers from said single stranded polynucleotide sequences, (5) hybridizing single stranded extended polynucleotide primers from said first complementary pair with said polynucleotide primer, (6) extending said polynucleotide primer along said single stranded extended polynucleotide primers to provide a second complementary pair of extended polynucleotide primers, (7) dissociating said second complementary pair of extended polynucleotide primers from said single stranded extended polynucleotide primers, and (8) repeating steps (5)–(7) above, wherein steps (a) and (b) are performed wholly or partially sequentially or concomitantly; and (c) detecting extended polynucleotide primers, the presence thereof indicating the presence of said polynucleotide analyte.

31. The method of claim 30 wherein said S2 is at least 60% complementary with each of said nucleotide sequences contiguous with the 3' ends of said complementary single stranded polynucleotide sequences.

32. The method of claim 30 wherein said single stranded polynucleotide sequences or said first or second extended polynucleotide primer is DNA.

33. The method of claim 30 wherein said polynucleotide primer is 24 to 90 nucleotides in length.

34. The method of claim 30 wherein said S2 contains at least one ambiguous nucleotide capable of binding to A, T, G and C.

35. The method of claim 34 wherein said ambiguous nucleotide is inosine.

36. The method of claim 30 wherein said S1 is at least 75% G and C.

37. The method of claim 30 wherein said S2 comprises a series of multiplets of nucleotides, said multiplets taken in order corresponding to at least 50% complementary multiplets at respectively ordered positions located alternately at a sequence contiguous with the 3' ends of each of said complementary single stranded polynucleotide sequences.

38. The method of claim 37 wherein said S2 consists solely of said multiplets.

39. The method of claim 37 wherein said multiplets are quartets.

40. The method of claim 30 wherein said template-dependent polynucleotide polymerase is a DNA polymerase and said nucleoside triphosphates are dATP, dGTP, dCTP, and dTTP.

41. The method of claim 30 wherein said method is carried out at at least a 100-fold excess concentration of said polynucleotide primer relative to the concentration of said polynucleotide analyte.

42. A method comprising repetition of steps (5)–(7) of claim 30 wherein the number of said copies of said single stranded polynucleotide sequences is increased by at least a factor of a thousand.

43. The method of claim 30 wherein said polynucleotide primer is labeled with a reporter group.

44. The method of claim 43 wherein said reporter group is selected from the group consisting of ligands, fluorescers, chemiluminescers, catalysts, co-enzymes, radioactive substances, amplifiable polynucleotide sequences, surfaces and small organic molecules.

45. The method of claim 30 wherein said single stranded polynucleotides contain a sequence that when hybridized to its complementary sequence can be bound specifically by a receptor.

46. The method of claim 45 wherein said receptor is selected from the group consisting of repressors, activators, and restriction enzymes.

47. The method of claim 30 wherein said detection includes detection of a specific DNA sequence.

48. The method of claim 30 comprising identifying complementary single stranded polynucleotide sequences of said analyte, together with nucleotide sequences contiguous with the 3' ends thereof, and preparing said polynucleotide primer.

* * * * *